United States Patent [19]

Newman

[11] Patent Number: 5,376,093
[45] Date of Patent: Dec. 27, 1994

[54] TIBIOFEMORAL ALIGNMENT GUIDE

[76] Inventor: Michael H. Newman, 9711 Arlene St., Anchorage, Ak. 99515

[21] Appl. No.: 987,745

[22] Filed: Dec. 9, 1992

[51] Int. Cl.⁵ .................................. A61B 5/103
[52] U.S. Cl. ............................ 606/88; 606/102; 128/774; 128/782; 33/511
[58] Field of Search ............ 606/53, 54, 86–89, 606/91, 96, 102; 128/782, 774; 33/512, 511, 514.2, 515, 534, 538; 623/20

[56] References Cited

U.S. PATENT DOCUMENTS

| | | | |
|---|---|---|---|
| 2,737,724 | 3/1956 | Herz | 606/89 |
| 4,349,018 | 9/1982 | Chambers . | |
| 4,487,203 | 12/1984 | Androphy . | |
| 4,567,885 | 2/1986 | Androphy . | |
| 4,567,886 | 2/1986 | Petersen . | |
| 4,621,630 | 11/1986 | Kenna . | |
| 4,759,350 | 7/1988 | Dunn et al. . | |
| 4,772,286 | 9/1988 | Goble et al. . | |
| 4,787,377 | 11/1988 | Laboureau . | |
| 4,944,760 | 7/1990 | Kenna . | |
| 4,959,066 | 9/1990 | Dunn et al. | 606/87 |
| 4,989,337 | 2/1991 | Mason et al. | 128/774 |
| 5,013,314 | 5/1991 | Firica et al. | 606/86 |
| 5,059,194 | 10/1991 | Michelson | 606/53 |
| 5,192,321 | 3/1993 | Strokon | 606/88 |
| 5,263,492 | 11/1993 | Voyce | 128/782 |

FOREIGN PATENT DOCUMENTS

| | | | |
|---|---|---|---|
| 1233386 | of 0000 | Canada . | |
| 2517698 | 10/1976 | Germany | 128/774 |
| 0424286 | 5/1967 | Switzerland | 33/534 |
| 0674576 | 6/1990 | Switzerland | 33/534 |
| 1175434 | 8/1985 | U.S.S.R. | 128/774 |
| 1225563 | 4/1986 | U.S.S.R. | 606/102 |
| 1284515 | 1/1987 | U.S.S.R. | 128/774 |

Primary Examiner—Stephen C. Pellegrino
Assistant Examiner—Jeffrey A. Schmidt
Attorney, Agent, or Firm—Bromberg & Sunstein

[57] ABSTRACT

A tibiofermoral alignment guide suitable for use during total knee replacement surgery, provides a means of measuring the angle subtended at the knee joint by the tibial axis relative to the femoral axis. The device can be repeatedly inserted into the medullary canal of the femur and removed therefrom during surgery. The device comprises a rigid rod being formed as an integral unit having tibial, intermediate and femoral segments, wherein the tibial and femoral segments are roughly parallel forming an approximately z-shaped guide.

12 Claims, 2 Drawing Sheets

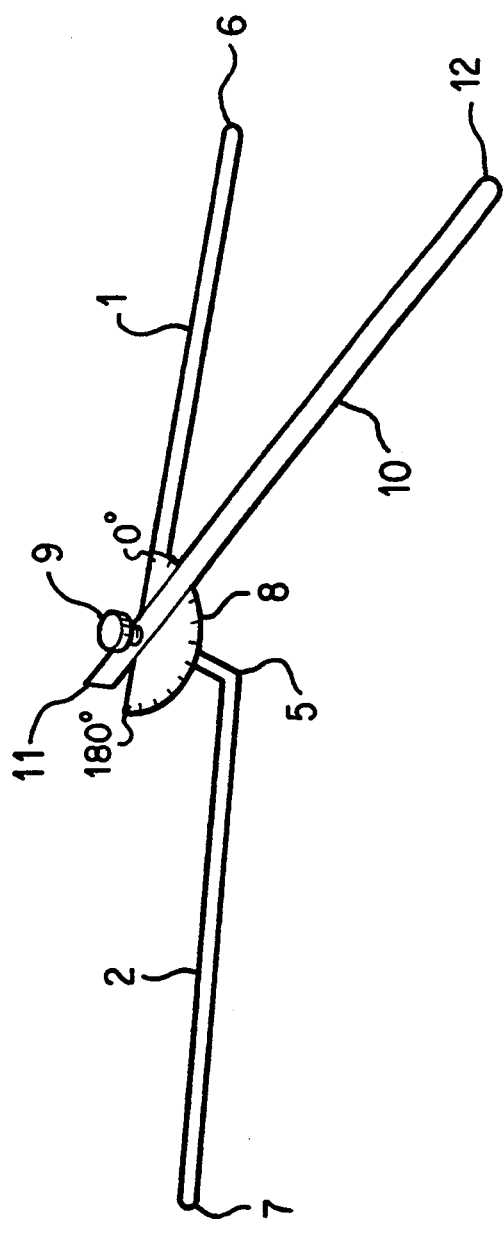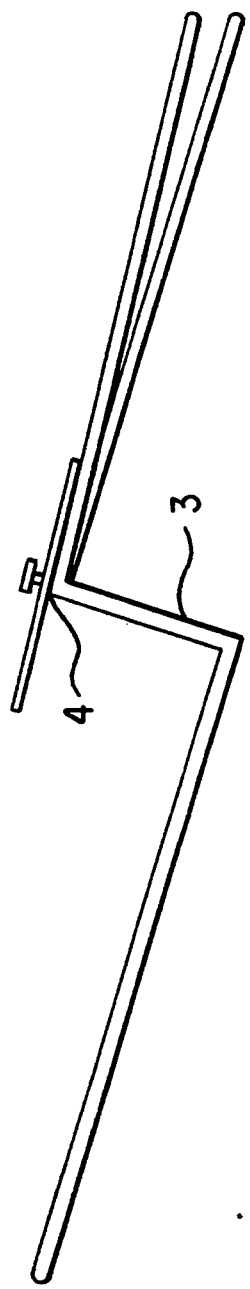

TIBIOFEMORAL ALIGNMENT GUIDE

TECHNICAL FIELD

This application relates generally to knee surgical techniques and more particularly to an apparatus and method for alignment of the knee joint during a knee prosthesis procedure.

BACKGROUND ART

Knee surgery for the repair and/or replacement of knee joints in a human subject has become a common place procedure. Total knee implants when properly installed will closely approximate or mimic natural knee movement. Heretofore, with the surgical instruments available, a surgeon installing an implant must have had a high degree of skill in order to achieve optimim fit and alignment.

The knee joint is formed between the condyles of the femur in the upper leg and the head of the tibia in the lower leg with the patella in front. The knee joint permits flexion and extension and in certain positions, a slight rotation inward and outward. This movement is not a simple hinge like motion but is a complicated movement consisting of a certain amount of gliding and rotation.

In order for the knee to function with the required range of movements, the alignment of femur to the tibia is of key importance. Incorrect alignment results in inappropriate contact between the femoral condyles and the tibia causing abnormal wear on contact points of the bone with resulting malfunction of the joint.

The alignment of the knee with respect to the hip and the ankle is determined by measuring the angle between the mechanical axis of the whole leg and the longitudinal axis of the femoral shaft, the angle being about 6°. The mechanical axis is defined as a straight line extending from the center of the hip, through the center of the knee to the center of the ankle along the tibial shaft forming an angle of approximately 3° to the vertical. In contrast, the femoral shaft meets meets the center of the knee at an angle of about 9° to the vertical, this angle varying according to body build. When the natural alignment of the knee joint is disrupted, subsequent joint instability, ligamental imbalance and excessive stress at fixation interfaces occurs. Correction of this type of damage necessitates in some cases a total surgical replacement of the knee joint. Just as the initial damage to the joint is caused by misalignment, the successful replacement of the knee joint calls for the optimum alignment of the prosthesis. At present, these alignment measurements commonly rely on indirect measurement of the angle between the longitudinal axis of the femoral shaft and the mechanical axis by measuring each angle relative to the vertical or horizontal axis (U.S. Pat. No. 4,349,018; U.S. Pat. No. 4,487,203).

The surgical procedure for knee joint replacement involves a series of steps that include opening up the knee joint, followed by the cutting and shaping of the proximal tibia and the distal femur and the subsequent insertion of commercially available knee prosthesis. The successful positioning of the prosthesis is dependent on all the preceding surgical steps. These steps not only include the proper alignment of the knee during the cutting and shaping of the bone prior to the application of the prosthesis but also on the proper alignment during placement and fixation of the prosthesis trials.

Because existing alignment procedures rely on alignment guides that form part of the drill jigs used to cut and shape bone (U.S. Pat. No. 4,759, U.S. Pat. No. 4,349,018; U.S. Pat. No. 4,487,203 and U.S. Pat. No. 4,567,885), no direct alignment measurement after removal of the jigs is possible. Thus, alignment of the femur and tibia may be determined during cutting the bone but not during subsequent fitment of the prosthetic device.

Guide rods of the prior art are fixed in the tibia or femur by drilling a plurality of holes into the bone of the tibia or femur and utilizing pins inserted into the holes to secure the guide. The guide rods of the prior art are secured throughout the procedure for cutting and shaping the femoral condyle and the tibial head. (U.S. Pat. No. 4,487,203; U.S. Pat. No. 4,567,885; U.S. Pat. No. 4,759,350; U.S. Pat. No. 4,349,018, U.S. Pat. No. 4,621,630). Indeed, the use of prior art alignment guides is restricted to the measurement of alignment during cutting and shaping of the femoral condyle and the tibial head. (U.S. Pat. No. 4,944,760; U.S. Pat. No. 4,621,630; U.S. Pat. No. 4,759,350) and cannot be used to check alignment of the knee during placement of the tibial and femoral trials. In some cases, separate and distinct tibial and femoral alignment guides are used, requiring holes to be drilled in the medullary canal of both the femur and the tibia of a subject. (U.S. Pat. No. 4,349,018; U.S. Pat. No. 4,567,885).

SUMMARY OF THE INVENTION

In accordance with the present invention, an improved tibiofemoral alignment guide, free of many disadvantages of the prior art, is provided. The tibiofemoral alignment guide for use in knee joint replacement surgery provides a direct measurement of the angle between the long axes of the femur and the tibia. The invention permits insertion and removal of the guide throughout the entire surgical procedure, and that the guide provides an accurate measure of the angle between the long axes of the tibia and the femur.

In a preferred embodiment, the guide comprises a rigid rod formed as an integral unit having tibial, intermediate and femoral segments. The guide of this embodiment has two ends, the first end of the femoral segment forming a first rod end and the second end of the femoral segment being affixed to the first end of the intermediate segment. The first end of the tibial segment forms a second rod end, the second end of the tibial segment being affixed to the second end of the intermediate segment. The femoral segment has a length and shape suitable for insertion into the medullary canal, thereby acting as a reference for the axis of the femoral shaft. The tibial segment has a length that is sifficient to permit measurement of the angle between the femoral and the tibial shaft external to the joint, the intermediate segment being of a length that displaces the tibial segment clear of the knee joint while remaining connected to the second end of the femoral segment.

In a preferred embodiment, the tibiofemoral alignment guide includes an arrangement for measuring the angle between the tibial shaft, tibial segment and the axis of the femoral shaft, such means comprising a goniometer affixed to the end of the intermediate segment at the junction with the tibial segment by means of a screw and an adjustable arm containing two straight edges comprising the inside and the outside edge suspended at the same point as the goniometer by means of the screw for measuring the angle with respect to the femur. In a preferred embodiment, the guide is formed from a rigid biocompatible material such as stainless steel.

In a preferred embodiment, the tibial-femoral alignment guide is so designed that the length of the intermediate segment is sufficient to clear the foreshortened distal limb of a tibial base plate trial used for spacing determinations during surgery on the knee joint.

The method for using the tibiofemoral guide having the above features includes inserting the first end of the rod into the medullary canal of the femur as the sole means of attachment of the alignment guide during alignment. The guide can be rotated about an axis coincident with the femoral segment to orient the intermediate segment so as to project the tibial segment outside the joint and measuring the angle subtended between the tibial segment and the tibial shaft. The tibiofemoral angle can be measured during surgery by repeatedly introducing the rod into the medullary canal for purposes of alignment for individual surgical procedures undertaken during knee replacement surgery and removing the rod subsequent to completing each measurement.

BRIEF DESCIPTION OF THE DRAWINGS

These and other objects will be apparent from the following detailed description in which preferred embodiments of the present invention and methods of use are described in detail in conjunction with the accompanying drawings.

FIG. 1 is a perspective view of a tibiofemoral alignment guide in accordance with a preferred embodiment of the invention, having a goniometer and arm.

FIG. 2 is a side view of the tibiofemoral alignment guide of FIG. 1.

DETAILED DESCRIPTION

Figure 4:
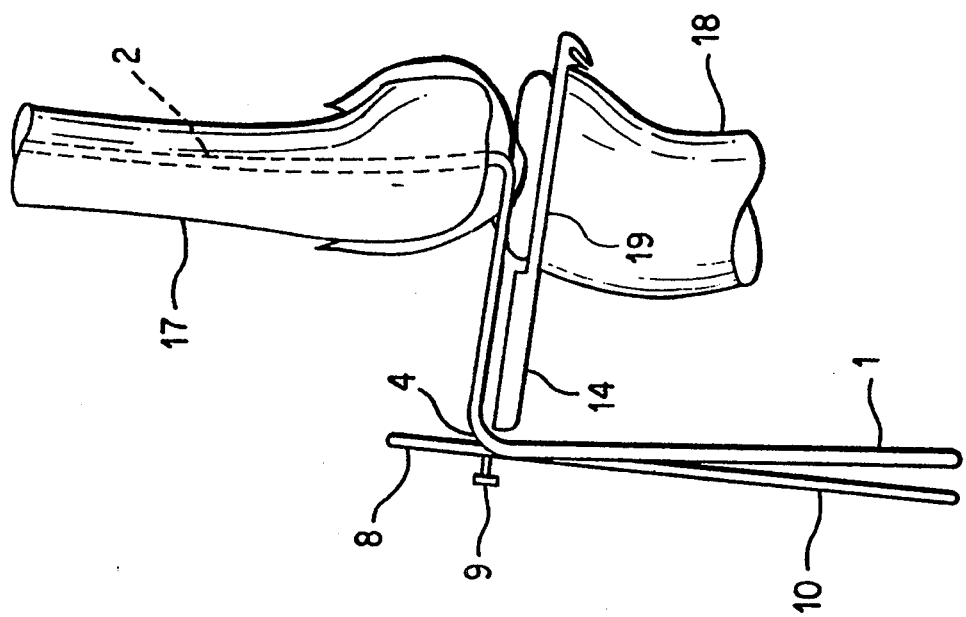
FIG. 4 is a side view of the tibiofemoral alignment guide of FIG. 1 positioned for aligning the knee with trials in place.

A preferred embodiment of an alignment guide in accordance with the present invention is shown in FIGS. 1 and 2. The alignment guide comprises a rigid rod having a diameter of about 0.2 inches made of a biocompatible material such as stainless steel. The guide has a tibial segment (1) and a femoral segment (2) joined by an intermediate segment (3). The tibial segment here subtends a right angle with the intermediate segment at the junction between the two segments (4) and the intermediate segment subtends a right angle with the femoral segment at the junction between the two segments (5). The femoral, intermediate and tibial segments lie in the same plane. The tibial segment here extends at least 12 inches between the junction with the intermediate segment and the tibial end (6), while the femoral segment extends about 12 inches from the junction with the intermediate segment to the femoral end (7).

Once the tibiofemoral alignment guide is in place, the angle between the tibial axis and femoral axis can be measured by any suitable angle measuring device that is either hand held or fixed to the device. In the specific embodiment shown in FIGS. 1 and 2, a goniometer (8) is pivotally secured by a screw (9) to the tibial segment, the goniometer being approximately placed at junction (4) and is oriented in a plane at right angles to the plane of the alignment device. The goniometer is marked with angle measurements from 0 to 1.80 degrees. An arm (10) is pivotably mounted on the goniometer with screw (9), the arm having a first end (11) and a second end (12) being available for alignment with the lateral midpoint of the ankle joint.

Figure 3:
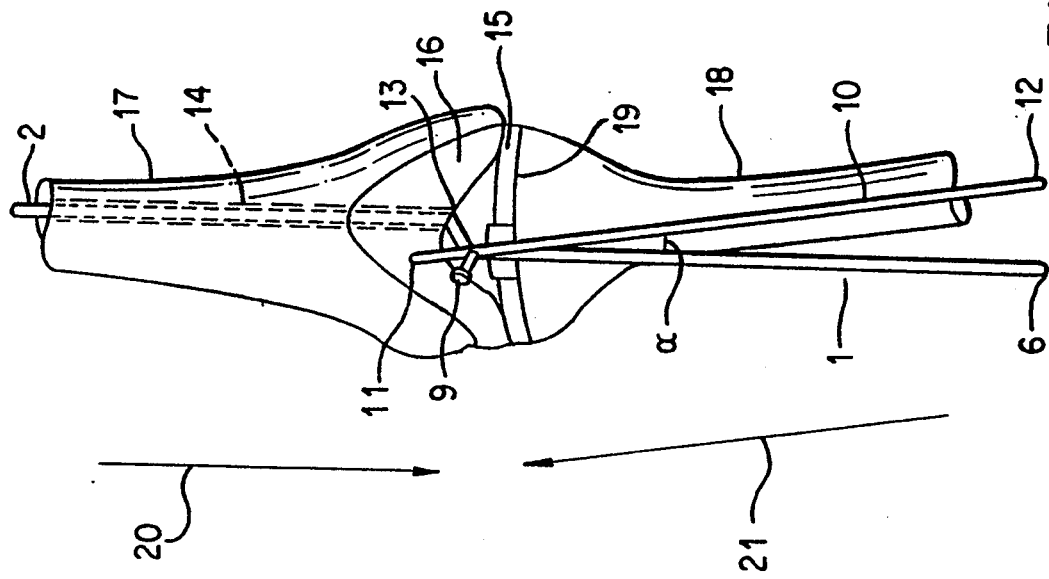
FIG. 3 is a front view of the embodiment of FIG. 1 positioned for aligning the knee with trials in place.

The positioning of the alignment guide in the knee is shown in FIGS. 3 and 4. An intramedullary drill hole (13) is made in the femur (17) to provide access to the femoral medullary canal (14) that extends along the femoral long axis (20). The femoral segment of the alignment guide (2) is passed up the medullary canal of the femur, while the knee is flexed at 90°. Subsequently, the leg may be straightened to reveal the intermediate segment (3) of the alignment guide projecting in a forward direction above the proximal knee and the tibial segment extending toward the ankle along the femoral long axis (20). The arm (10) is then adjusted by rotation so that end (12) is pointing to the midpoint of the ankle along the tibial axis (20). The angle subtended by the arm end (12) from the axis of the tibial segment can then be measured on the goniometer (8). The optimal angle is determined for each patient in the preoperative planning process by examining X-ray photographs of the femur. Commonly the angle between the tibial axis (21) that extends along the tibial shaft (18) and the long axis of the femur (20) is approximately 6°. In some individuals, this angle may be as much as 9° and in other patients it may be as little as 3° when properly aligned. The alignment guide thus provides the appropriate alignment of the knee joint for each patient as predetermined.

The alignment guide can be readily withdrawn and replaced during the surgical procedure. The procedure occurs in three phases. In the first phase, incisions are made to expose the joint and an intramedullary hole (13) is made for access to the intramedullary canal. The guide is inserted to measure the initial angle between the long axes of the tibia and femur, an angle which is commonly distorted in a damaged joint.

The second phase requires the cutting and shaping of the tibial head and femoral condyle in preparation for the insertion of the trials. In addition to using a tibial cutting jig to line up the femoral cut, the tibiofemoral alignment device may be utilized to confirm the angle of the femoral cut prior to forming the tibial cut. Subsequently. the tibial cut surface and the femoral cut surface are pushed against each other and the tibiofemoral alignment guide is again used to determine the angle between the tibial and femoral axes.

The third phase requires the placement of trial components on the tibia (15 ) and (19) and femoral condyle (16) for the purposes of adjustment prior to placement of the prosthetic device. At this time, the angle between the femoral and tibial axes must be correctly adjusted to be about 6 degrees. It is therefore advantageous to utilize the alignment device with the tibial and femoral baseplate trials in place is shown in FIG. 3 and 4. The trials may be modified before use by enlarging the intercondylar notch area on the femoral trial to allow access to the intramedullary hole in the femur and modifying the baseplate trial having a projecting handle (14) so that the handle (14) does not interfere with the tibial segment (1) of the guide.

While the invention is illustrated and described by means of specific embodiments, it is to be understood that numerous changes and modifications may be made therein without departing from the spirit and scope of the invention as defined in the appended claims.

What is claimed is:

1. A tibiofemoral alignment guide suitable for measuring an angle between the axis of femoral and tibial bones at a knee joint, comprising:
   (a) a femoral segment joined to an intermediate segment, the intermediate segment being joined to a tibial segment, wherein the femoral segment is removably inserted at the knee into the femoral medullary canal and the tibial segment extends external to the tibial bone and in a direction away from the knee joint;
   (b) the femoral segment having a diameter and a length suitable for maintaining the femoral segment within the femur without physical attachment therein, such that the alignment guide serves to align the tibia and femur and can be readily inserted or removed during knee surgery;
   (c) a measurement means for determining the angle between the axis of the tibial shaft and the axis of the femoral shaft.

2. A tibiofemoral alignment guide comprising: a rigid rod, being formed as an integral unit having tibial, intermediate and femoral segments, each segment having a pair of ends, wherein;
   (a) the tibial and femoral segments being generally straight and at least roughly parallel to each other so that the segments collectively form an approximately Z-shaped guide,
   (b) a first end of the femoral segment forming a first rod end, a second end of the femoral segment being affixed to a first end of the intermediate segment, a first end of the tibial segment forming a second rod end, a second end of the tibial segment being affixed to a second end of the intermediate segment;
   (c) a first angle subtended by the tibial and intermediate segments substantially equaling a second angle subtended by the intermediate and femoral segments;
   (d) the femoral segment having a length and a shape compatible with the length and shape of the medullary canal, suitable for repeated insertion into the medullary canal and removal therefrom, thereby acting as a reference for the axis of the femoral shaft;
   (e) the tibial segment being external to the tibia, having a length sufficient to permit angular measurement between the tibial segment and the tibia;
   (f) the intermediate segment having a length that displaces the tibial segment clear of the knee joint while remaining connected to the second end of the femoral segment; and
   (f) a measurement means for determining the angle between the axis of the tibial shaft and the axis of the femoral shaft.

3. A guide in accordance with claim 2, wherein the angle subtended by the tibial and intermediate segments and by the intermediate and femoral segments is approximately 90 degrees.

4. A guide in accordance with claim 2, wherein the measurement means includes a goniometer.

5. A guide in accordance with claim 4, wherein the goniometer has a zero mark that is aligned with the tibial segment.

6. A guide in accordance with claim 5, further comprising a mounted arm that is pivotable about an axis approximately coincident with that of the intermediate segment, thereby providing an arrangement for indicating the angle of the tibia when the arm is aligned with it.

7. A guide in accordance with claim 2, wherein the rod is made of stainless steel.

8. A guide in accordance with claim 2, wherein the length of the intermediate segment is sufficient to clear the distal limb of a tibial base plate trial used for spacing determinations during surgery on the knee joint.

9. A guide according to claim 2, wherein the tibial segment has a length of approximately 12 inches.

10. A guide according to claim 2, wherein the femoral segment has a length of approximately 12 inches.

11. A method of directly measuring the tibiofemoral angle during total knee replacement surgery in a human subject comprising:
   (A) providing a rigid rod being formed as an integral unit having tibial, intermediate and femoral segments, each segment having a pair of ends, wherein the tibial and femoral segments being generally straight and at least roughly parallel to each other so that the segments collectively form an approximately Z-shaped guide
   (B) inserting the first end of the rod into the medullary canal of the femur and rotating the rod about an axis coincident with the femoral segment to orient the intermediate segment so as to project the tibial segment outside the joint; and
   (C) measuring the angle subtended between the tibial segment and tibial shaft using a goniometer, the goniometer being fixed at the junction between the tibial segment and the intermediate segment, and the angle being measured using an arm extending pivotally from the goniometer.

12. A method according to claim 11, further comprising:
   (D) repeatedly introducing the rod into the medullary canal for purposes of alignment for individual surgical procedures undertaken during knee replacement surgery and removing the rod subsequent to completing each measurement.

* * * * *